United States Patent
Mate et al.

(10) Patent No.: US 9,943,704 B1
(45) Date of Patent: Apr. 17, 2018

(54) METHOD AND SYSTEM FOR FIDUCIALS CONTAINED IN REMOVABLE DEVICE FOR RADIATION THERAPY

(75) Inventors: Timothy P. Mate, Bellevue, WA (US); Tricia V. Zeller, Normandy Park, WA (US); Steven C. Dimmer, Bellevue, WA (US); Fergus Quigley, Seattle, WA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 546 days.

(21) Appl. No.: 12/563,084

(22) Filed: Sep. 18, 2009

Related U.S. Application Data (60) Provisional application No. 61/146,257, filed on Jan. 21, 2009.

(51) Int. Cl.
| | | |
|---|---|---|
| A61N 5/00 | (2006.01) | |
| A61N 5/10 | (2006.01) | |
| A61B 90/10 | (2016.01) | |
| A61B 90/00 | (2016.01) | |
| A61B 34/20 | (2016.01) | |

(52) U.S. Cl.
CPC .......... *A61N 5/1049* (2013.01); *A61B 34/20* (2016.02); *A61N 5/1014* (2013.01); *A61B 2034/2051* (2016.02); *A61B 2090/101* (2016.02); *A61B 2090/3958* (2016.02); *A61N 2005/1051* (2013.01)

(58) Field of Classification Search
CPC .......... A61N 2005/1051; A61N 5/1049; A61N 5/107; A61N 5/1067; A61N 2005/105; A61N 5/1039; A61N 5/1014; A61N 5/1048; A61B 2090/3958; A61B 2034/2051; A61B 34/20; A61B 2034/2072; A61B 34/25; A61B 2034/301; A61B 2090/101; A61B 2090/363; A61B 2090/374; A61B 2090/3975; A61B 2090/3995; A61B 34/30; A61B 90/14; A61B 90/16; A61B 90/39
USPC ................ 600/420, 424, 426, 431, 432, 458
See application file for complete search history.

(56) References Cited

U.S. PATENT DOCUMENTS

| | | | |
|---|---|---|---|
| 3,967,161 A | 6/1976 | Lichtblau | |
| 4,023,167 A | 5/1977 | Wahlstrom | |
| 4,114,601 A | 9/1978 | Abels | |

(Continued)

FOREIGN PATENT DOCUMENTS

| | | | |
|---|---|---|---|
| WO | 9603925 A1 | 2/1996 | |
| WO | 0016686 A2 | 3/2000 | |

(Continued)

*Primary Examiner* — Ruth S Smith
(74) *Attorney, Agent, or Firm* — Perkins Coie LLP (57) ABSTRACT

Method and system fiducials contained in removable a device for use in guided radiation therapy treatment. One embodiment includes an active marker configured to be pre-loaded into a catheter for removeably implanting in the tissue of a patient. Another embodiment of the implantable device includes a stability element coupled to the marker and further coupled to an explant line. In some embodiments, the stability element is configured to hold the marker at a fixed location within the catheter (e.g., known location) with respect to a target in the tissue. In other embodiments, the explant line has a first portion coupled to the marker and/or the stability element and a second portion configured to be at least proximate to the dermis of the patient.

15 Claims, 5 Drawing Sheets

(56) References Cited

U.S. PATENT DOCUMENTS

| | | |
|---|---|---|
| 4,123,749 A | 10/1978 | Hartmann et al. |
| 4,127,110 A | 11/1978 | Bullara |
| 4,160,971 A | 7/1979 | Jones et al. |
| 4,222,374 A | 9/1980 | Sampson et al. |
| 4,260,990 A | 4/1981 | Lichtblau |
| 4,393,872 A | 7/1983 | Reznik et al. |
| 4,618,822 A | 10/1986 | Hansen |
| 4,633,250 A | 12/1986 | Anderson, III et al. |
| 4,643,196 A | 2/1987 | Tanaka et al. |
| 4,653,496 A | 3/1987 | Bundy et al. |
| 4,696,287 A | 9/1987 | Hortmann |
| 4,795,995 A | 1/1989 | Eccleston et al. |
| 4,799,495 A | 1/1989 | Hawkins et al. |
| 4,909,789 A | 3/1990 | Taguchi et al. |
| 4,936,823 A | 6/1990 | Colvin et al. |
| 4,945,914 A | 8/1990 | Allen |
| 4,994,079 A | 2/1991 | Genese et al. |
| 5,031,634 A | 7/1991 | Simon |
| 5,062,847 A | 11/1991 | Barnes |
| 5,095,224 A | 3/1992 | Renger |
| 5,099,845 A | 3/1992 | Besz et al. |
| 5,107,862 A | 4/1992 | Fabian |
| 5,142,292 A | 8/1992 | Chang |
| 5,170,055 A | 12/1992 | Carroll et al. |
| 5,325,873 A | 7/1994 | Hirschi et al. |
| 5,353,804 A | 10/1994 | Kornberg et al. |
| 5,409,004 A | 4/1995 | Sloan |
| 5,423,334 A | 6/1995 | Jordan |
| 5,423,744 A | 6/1995 | Gencheff et al. |
| 5,425,367 A | 6/1995 | Shapiro et al. |
| 5,425,382 A | 6/1995 | Golden et al. |
| 5,431,161 A | 7/1995 | Ryals et al. |
| 5,446,548 A | 8/1995 | Gerig et al. |
| 5,509,900 A | 4/1996 | Kirkman |
| 5,528,651 A | 6/1996 | Leksell et al. |
| 5,626,630 A | 5/1997 | Markowitz et al. |
| 5,638,819 A | 6/1997 | Manwaring |
| 5,651,043 A | 7/1997 | Tsuyuki et al. |
| 5,680,106 A | 10/1997 | Schrott et al. |
| 5,697,384 A | 12/1997 | Miyawaki |
| 5,707,362 A | 1/1998 | Yoon |
| 5,707,390 A | 1/1998 | Bonutti |
| 5,711,299 A | 1/1998 | Manwaring |
| 5,727,552 A | 3/1998 | Ryan |
| 5,735,795 A | 4/1998 | Young et al. |
| 5,748,767 A | 5/1998 | Raab |
| 5,754,623 A | 5/1998 | Seki |
| 5,757,881 A | 5/1998 | Hughes |
| 5,764,052 A | 6/1998 | Renger |
| 5,769,861 A | 6/1998 | Vilsmeier |
| 5,810,851 A | 9/1998 | Yoon |
| 5,815,076 A | 9/1998 | Herring |
| 5,840,148 A | 11/1998 | Campbell et al. |
| 5,868,673 A | 2/1999 | Vesely |
| 5,879,297 A | 3/1999 | Haynor et al. |
| 5,902,310 A | 5/1999 | Foerster et al. |
| 5,910,144 A | 6/1999 | Hayashi |
| 5,911,717 A | 6/1999 | Jacobsen et al. |
| 5,928,137 A | 7/1999 | Green |
| 5,941,890 A | 8/1999 | Voegele et al. |
| 5,951,481 A | 9/1999 | Evans |
| 5,951,514 A | 9/1999 | Sahota |
| 5,957,934 A | 9/1999 | Rapoport |
| 5,989,265 A | 11/1999 | Bouquet De La Joliniere |
| 6,026,818 A | 2/2000 | Blair |
| 6,059,734 A | 5/2000 | Yoon |
| 6,061,644 A | 5/2000 | Leis |
| 6,066,158 A | 5/2000 | Engelson et al. |
| 6,067,465 A | 5/2000 | Foo et al. |
| 6,076,008 A | 6/2000 | Bucholz |
| 6,081,238 A | 6/2000 | Alicot |
| 6,082,366 A | 7/2000 | Andra et al. |
| 6,144,875 A | 11/2000 | Schweikard et al. |
| 6,161,009 A | 12/2000 | Skurdal et al. |
| 6,198,963 B1 | 3/2001 | Haim et al. |
| 6,220,248 B1 | 4/2001 | Voegele et al. |
| 6,222,544 B1 | 4/2001 | Tarr et al. |
| 6,228,055 B1 | 5/2001 | Foerster et al. |
| 6,234,177 B1 | 5/2001 | Barsch |
| 6,246,900 B1 | 6/2001 | Cosman et al. |
| 6,272,371 B1 | 8/2001 | Shlomo |
| 6,307,473 B1 | 10/2001 | Zampini et al. |
| 6,325,758 B1 | 12/2001 | Carol et al. |
| 6,336,904 B1 | 1/2002 | Nikolchev |
| 6,353,655 B1 | 3/2002 | Siochi |
| 6,356,782 B1 | 3/2002 | Sirimanne et al. |
| 6,359,959 B1 | 3/2002 | Butler et al. |
| 6,360,116 B1 | 3/2002 | Jackson, Jr. et al. |
| 6,363,940 B1 | 4/2002 | Krag |
| 6,371,379 B1 | 4/2002 | Dames et al. |
| 6,371,904 B1 | 4/2002 | Sirimanne et al. |
| 6,377,162 B1 | 4/2002 | Delestienne et al. |
| 6,381,485 B1 | 4/2002 | Hunter et al. |
| 6,385,286 B1 | 5/2002 | Fitchard et al. |
| 6,385,288 B1 | 5/2002 | Kanematsu |
| 6,393,096 B1 | 5/2002 | Carol et al. |
| 6,405,072 B1 | 6/2002 | Cosman |
| 6,416,520 B1 | 7/2002 | Kynast et al. |
| 6,425,903 B1 | 7/2002 | Voegele |
| 6,447,448 B1 | 9/2002 | Ishikawa et al. |
| 6,498,944 B1 | 12/2002 | Ben-Haim et al. |
| 6,501,981 B1 | 12/2002 | Schweikard et al. |
| 6,535,756 B1 | 3/2003 | Simon et al. |
| 6,574,492 B1 | 6/2003 | Ben-Haim et al. |
| 6,638,231 B2 | 10/2003 | Govari et al. |
| 6,654,629 B2 | 11/2003 | Montegrande |
| 6,675,810 B2 | 1/2004 | Krag |
| 6,698,433 B2 | 3/2004 | Krag |
| 6,725,083 B1 | 4/2004 | Burbank et al. |
| 6,766,186 B1 | 7/2004 | Hoyns et al. |
| 6,812,842 B2 | 11/2004 | Dimmer |
| 6,822,570 B2 | 11/2004 | Dimmer et al. |
| 6,838,990 B2 | 1/2005 | Dimmer |
| 6,918,919 B2 | 7/2005 | Krag |
| 6,934,356 B1 | 8/2005 | Satheesan et al. |
| 6,937,696 B1 | 8/2005 | Mostafavi |
| 6,977,504 B2 | 12/2005 | Wright et al. |
| 6,993,375 B2 | 1/2006 | Burbank et al. |
| 6,999,555 B2 | 2/2006 | Morf |
| 7,026,927 B2 | 4/2006 | Wright et al. |
| 7,027,707 B2 | 4/2006 | Imaki |
| 7,044,957 B2 | 5/2006 | Foerster et al. |
| 7,047,063 B2 | 5/2006 | Burbank et al. |
| 7,135,978 B2 | 11/2006 | Gisselberg et al. |
| 7,142,905 B2 | 11/2006 | Slayton et al. |
| 7,174,201 B2 | 2/2007 | Govari et al. |
| 7,176,798 B2 | 2/2007 | Dimmer et al. |
| 7,206,626 B2 | 4/2007 | Quaid, III |
| 7,206,627 B2 | 4/2007 | Abovitz et al. |
| 7,213,009 B2 | 5/2007 | Pestotnik et al. |
| 7,221,733 B1 | 5/2007 | Takai et al. |
| 7,229,417 B2 | 6/2007 | Foerster et al. |
| 7,280,863 B2 | 10/2007 | Shacher |
| 7,289,839 B2 | 10/2007 | Dimmer et al. |
| 7,318,805 B2 | 1/2008 | Schweikard et al. |
| 7,397,364 B2 | 7/2008 | Govari |
| 7,447,643 B1 | 11/2008 | Olson et al. |
| 7,534,252 B2 | 5/2009 | Sepetka |
| 7,535,363 B2 | 5/2009 | Gisselberg et al. |
| 7,558,616 B2 | 7/2009 | Govari et al. |
| 7,565,191 B2 | 7/2009 | Burbank et al. |
| 7,590,441 B2 | 9/2009 | Govari |
| 7,599,730 B2 | 10/2009 | Hunter et al. |
| 7,606,405 B2 | 10/2009 | Sawyer et al. |
| 7,625,397 B2 | 12/2009 | Foerster et al. |
| 7,657,301 B2 | 2/2010 | Mate et al. |
| 7,657,302 B2 | 2/2010 | Mate et al. |
| 7,657,303 B2 | 2/2010 | Mate et al. |
| 7,668,582 B2 | 2/2010 | Sirimanne et al. |
| 7,696,876 B2 | 4/2010 | Dimmer |
| 7,729,742 B2 | 6/2010 | Govari |
| 7,778,687 B2 | 8/2010 | Dimmer et al. |
| 7,780,973 B2 | 8/2010 | Freeman et al. |
| 7,912,529 B2 | 3/2011 | Herron et al. |

(56) References Cited

U.S. PATENT DOCUMENTS

| | | |
|---|---|---|
| 8,046,052 B2 | 10/2011 | Verard et al. |
| 8,060,185 B2 | 11/2011 | Hunter et al. |
| 8,196,589 B2 | 6/2012 | Gisselberg |
| 8,239,002 B2 | 8/2012 | Neustadter et al. |
| 8,239,005 B2 | 8/2012 | Wright et al. |
| 8,277,391 B2 | 10/2012 | Foerster |
| 8,306,602 B2 | 11/2012 | Sirimanne |
| 8,320,993 B2 | 11/2012 | Sirimanne |
| 8,320,994 B2 | 11/2012 | Sirimanne |
| 8,401,616 B2 | 3/2013 | Verard |
| 8,452,375 B2 | 5/2013 | Krag |
| 8,467,853 B2 | 6/2013 | Hunter |
| 8,549,960 B2 | 10/2013 | Hoff |
| 2002/0065461 A1 | 5/2002 | Cosman |
| 2002/0083951 A1* | 7/2002 | Stegmaier et al. ........... 128/903 |
| 2002/0107437 A1 | 8/2002 | Sirimanne et al. |
| 2002/0165443 A1 | 11/2002 | Mori |
| 2002/0193685 A1 | 12/2002 | Mate et al. |
| 2003/0023161 A1 | 1/2003 | Govari et al. |
| 2003/0181794 A1* | 9/2003 | Rini .................. A61B 5/0031 600/300 |
| 2003/0192557 A1 | 10/2003 | Krag et al. |
| 2003/0206610 A1 | 11/2003 | Collins |
| 2003/0206614 A1 | 11/2003 | Kendrick et al. |
| 2004/0024304 A1 | 2/2004 | Foerster et al. |
| 2004/0068182 A1 | 4/2004 | Misra |
| 2005/0059888 A1 | 3/2005 | Sirimanne et al. |
| 2005/0080338 A1 | 4/2005 | Sirimanne et al. |
| 2005/0080339 A1 | 4/2005 | Sirimanne et al. |
| 2005/0085895 A1 | 4/2005 | Brown et al. |
| 2005/0101824 A1* | 5/2005 | Stubbs ................ A61N 5/1015 600/3 |
| 2005/0113855 A1* | 5/2005 | Kennedy et al. ............. 606/185 |
| 2005/0165305 A1 | 7/2005 | Foerster et al. |
| 2005/0182319 A1 | 8/2005 | Glossop |
| 2005/0273002 A1 | 12/2005 | Goosen et al. |
| 2006/0074443 A1 | 4/2006 | Foerster et al. |
| 2006/0093089 A1* | 5/2006 | Vertatschitsch et al. ....... 378/65 |
| 2006/0094923 A1* | 5/2006 | Mate .................................. 600/3 |
| 2008/0021308 A1 | 1/2008 | Dimmer et al. |
| 2008/0287781 A1* | 11/2008 | Revie .................... A61B 90/36 600/426 |
| 2009/0259284 A1 | 10/2009 | Yamasaki et al. |
| 2009/0278689 A1 | 11/2009 | Gisselberg et al. |
| 2009/0299174 A1 | 12/2009 | Wright et al. |

FOREIGN PATENT DOCUMENTS

| | | | |
|---|---|---|---|
| WO | 0239917 A1 | 5/2002 | |
| WO | 204061460 A2 | 7/2004 | |
| WO | WO 2005067792 A1 * | 7/2005 | ......... A61B 5/04001 |
| WO | WO 2006020377 A2 * | 2/2006 | |

\* cited by examiner

METHOD AND SYSTEM FOR FIDUCIALS CONTAINED IN REMOVABLE DEVICE FOR RADIATION THERAPY

CROSS-REFERENCE TO RELATED APPLICATION

This application claims priority to U.S. Provisional Application Ser. No. 61/146,257, filed on Jan. 21, 2009, entitled "METHOD AND SYSTEM FOR REMOVABLE FIDUCIALS FOR RADIATION THERAPY," which is hereby incorporated herein in its entirety by reference.

TECHNICAL FIELD

The present invention is related to radiation oncology and, more specifically, to accurately determining the location of a target for delivering external radiation.

BACKGROUND

Cancer begins in the cells of the patient and forms malignant tumors that are often treated by surgical resection. Such surgical treatments attempt to remove as much of a tumor as possible, but cancerous cells infiltrate into the tissue adjacent the tumor such that there is no clear boundary. Also, certain procedures seek to limit the treatment margin around the tumor to reduce the amount of healthy tissue removed from the patient. In breast cancer, for example, patients prefer to limit the size of the lumpectomy resection to avoid excessive reduction or non-uniformities of the breast. Both of these factors limit the efficacy of surgical procedures for treating cancer. As such, radiation therapy has become a significant and highly successful process for treating breast cancer, lung cancer, brain cancer and many other types of localized cancers. Radiation therapy is particularly useful for treating (a) tissue after resecting a tumor, (b) centrally located tumors, and/or (c) small cell tumors that cannot be surgically resected. Radiation therapy can also be used as a palliative treatment when a cure is not possible.

Breast cancer has recently been treated by surgically resecting cancerous breast tissue and subsequently treating the remaining tissue surrounding the resection cavity using radiation. Proxima Corporation and Xoft, Inc. have developed breast brachytherapy devices and systems for selectively irradiating the portion of the tissue surrounding the resection cavity created by a lumpectomy. The existing breast brachytherapy devices have a balloon configured to be implanted in the cavity within the breast and an internal radiation source that can be placed within the balloon. After performing a lumpectomy, the balloon is inserted into the surgical cavity and inflated until the balloon presses against the tissue. The balloon is typically left in the patient for approximately five days over which two radiation treatments per day are performed. Each radiation treatment includes inserting the radiation source into the balloon and activating the radiation source to deliver ionizing radiation for approximately 10-15 minutes. After all of the radiation treatments have been performed during the multi-day course of treatment, the balloon is deflated and removed from the patient.

Breast brachytherapy procedures, however, can be challenging. For example, it may be difficult to determine whether the balloon has been inflated accurately and to monitor the balloon to ensure that the balloon has maintained the desired size throughout the multi-day course of treatment. The size of the balloon is currently determined by instilling radiopaque contrast into the balloon and measuring a resulting CT or X-ray image using a ruler. The patient must accordingly undergo a CT scan or another type of X-ray to obtain the image, and then a practitioner must evaluate the image to determine if the balloon is at the desired size. This is time-consuming and expensive, and it should be performed each day during the course of treatment. This process also exposes the patient to additional radiation.

Breast brachytherapy may also have disadvantages associated with using an internal radiation source. For example, the balloon may move within the lumpectomy cavity over the course of treatment, which can cause the internal radiation source to over irradiate some areas and under irradiate other areas. Many existing systems do not detect the relative position between the balloon and the breast to mitigate this problem. Moreover, when the radiation source is asymmetrically positioned within the balloon (e.g., spaced apart from a rotational center line of the balloon), the rotational orientation of the balloon within the lumpectomy cavity can cause the radiation source to be located at an undesirable position relative to the tissue. Conventional techniques also do not identify the rotational orientation of the balloon. This can be problematic because the balloon can move after it has been implanted over the course of treatment, or the balloon may not inflate as planned. Conventional breast brachytherapy systems are also relatively large because they must contain both a balloon and an internal radiation source. Many patients are not comfortable with having a radiation source within their body or with having a large catheter projecting from their body for a number of days, and therefore a sizable number of patients elect not to undergo breast brachytherapy.

In light of the challenges associated with breast brachytherapy procedures, partial breast irradiation using an external radiation beam has been proposed. Although radiation beams, such as Three-Dimensional Conformal Radiation Therapy beams, can shape radiation beams to conform to the target tissue, it is still difficult to use external beam radiation to treat the tissue around the resection cavities in many applications. For example, the size and shape of the cavity may change over the multi-day period typically required for external beam radiation treatments, or the treatment target may move during the treatment sessions. As such, there is a need for improving external beam radiation for partial breast irradiation and other procedures that seek to irradiate controlled treatment margins around resection cavities.

BRIEF DESCRIPTION OF THE DRAWINGS

FIGS. 1-12 are illustrations of aspects of the method and system of removable fiducials for radiation therapy in accordance with embodiments of the current invention.

DETAILED DESCRIPTION

Overview

This outlines the devices and methods for a system to enable the use of removable fiducials for radiation therapy. Specific details of several embodiments of the disclosure are described below with reference to implantable devices and methods for external beam radiation treatments. Although many of the embodiments are described below with respect to partial breast irradiation systems and procedures for treating resection cavities, the systems and implantable devices can be used in other procedures for treating other indications. Moreover, several other embodiments of the invention can have different configurations, components, or procedures than those described in this section. For instance, the apparatus and methods can have one or more markers or other components for use in external beam radiation therapy procedures as described in U.S. patent application Ser. No. 11/165,843, filed on 24 Jun. 2005, and Ser. No. 11/166,801, filed on 24 Jun. 2005, PCT Application No. PCT/US08/70682, filed on Jul. 21, 2008, all of which are incorporated herein in their entirety by reference. In other instances, well-known structures associated with target locating and tracking systems have not been shown or described in detail to avoid unnecessarily obscuring descriptions of the embodiments of the invention. A person of ordinary skill in the art, therefore, will accordingly understand that the invention may have other embodiments with additional elements, or the invention may have other embodiments without several of the features shown and described below with reference to FIGS. 1-10E.

One embodiment of an implantable device for guided radiation therapy comprises an active marker having a circuit configured to be contained in an external sheath which is implanted in a patient and to transmit a wirelessly transmitted location signal from within the patient in response to a wirelessly transmitted source energy. In an alternative embodiment, the active marker transmits a location signal along a wire. The implantable device can further include a fastening unit for retaining the marker in a fixed position in the external sheath. The marker, for example, can comprise a leadless marker having a circuit with a core and a coil around the core.

Another embodiment of an implantable device for guided radiation therapy comprises an active marker configured to be pre-loaded into a catheter; the catheter is configured to be removeably implanted in the tissue of a patient. The marker transmits a non-ionizing wireless signal in response to a non-ionizing wirelessly transmitted source energy. The implantable device can further include a stability element coupled to the marker and an explant line. The stability element is configured to hold the marker at fixed location within the catheter (e.g., known location) with respect to a target in the tissue. The explant line has a first portion coupled to the marker and/or the stability element and a second portion configured to be at least proximate to the dermis of the patient.

Another embodiment of an implantable device for guided radiation therapy comprises an active marker configured to be positioned within a capsule configured to be implanted in a cavity of a patient, and to transmit a non-ionizing wireless signal in response to a non-ionizing wirelessly transmitted source energy. The device further includes a fastening unit coupled to the active marker and configured to (a) hold the marker at a desired location in the removable implant and (b) recognize deformation of the tissue cavity.

1. Embodiments of Localization Systems and Implantable Devices

Figure 1:
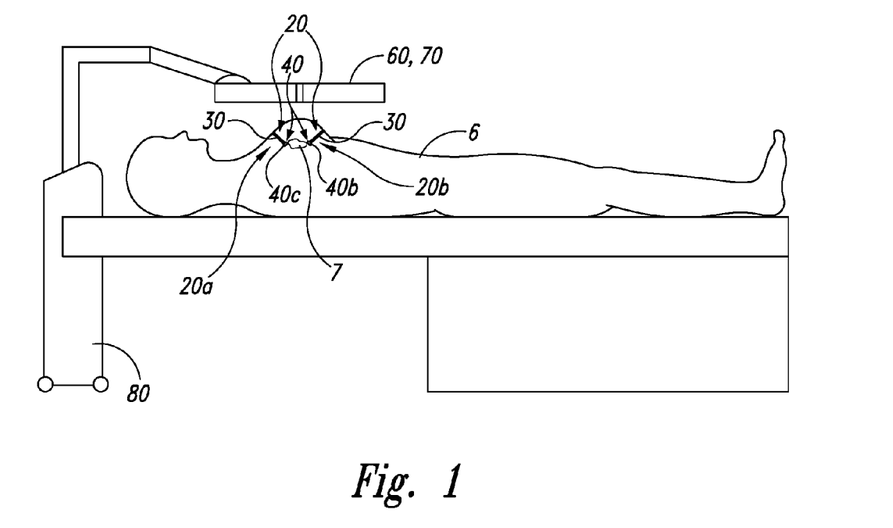
FIG. 1 is a side view of a localization system with a removable implantable device configured in accordance with embodiments of the present technology.
Figure 2:
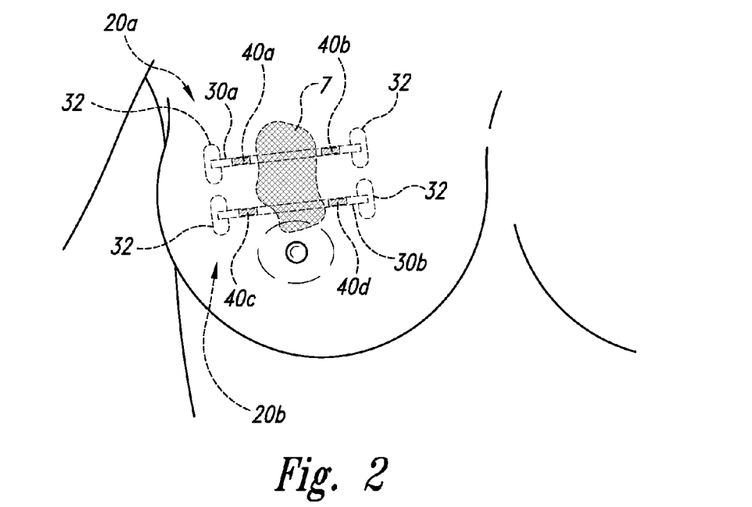
FIG. 2 is a front view of the removable implantable device of FIG. 1 implanted in a resection cavity in accordance with embodiments of the present technology.

FIG. 1 is a side view of a localization system 10 with an implantable device 20 (identified separately by reference numbers 20a and 20b) for facilitating radiation treatment of a target in accordance with an embodiment of the invention. FIG. 2 is a front view of the removable implantable device 20 of FIG. 1 implanted in a resection cavity in accordance with another embodiment of the present technology. As shown in FIG. 1, the implantable device 20 includes a sheath 30 having a distal tip configured to be inserted into the patient and a second end configured to be outside of the patient. The sheath 30 can be a catheter, such as a multilumen silicon catheter, or other type of device that can be percutaneously inserted into the breast or other part of the body. The implantable device 20 further includes a plurality of markers 40 (identified individually as first through fourth markers 40a-40d in FIG. 2; only second and third markers 40b and 40c are visible in FIG. 1). The markers 40 can comprise wired sensors configured to transmit independent location signals in response to an energy source that is external to the body, and/or one or more of the markers 40 can comprise wired transmitters that transmit source energy to a sensor array that is external to the body. For example, the active markers 40 can be single coil or multiple coil sensors that produce an electrical current in response to the strength of an externally supplied alternating magnetic field. Alternatively, one or more of the active markers can be a wireless active sensor that wirelessly transmits location signals in response to wirelessly transmitted excitation signals. Such wireless active markers can comprise a casing and a magnetic transponder in the casing as described in U.S. patent application Ser. No. 11/243,478 filed Nov. 14, 2015 and Ser. No. 11/166,801 filed Jun. 24, 2005, both of which are incorporated herein by reference in their entirety.

As further shown in the above-referenced applications, the localization system 10 can determine the location of the active markers 40 in real-time to facilitate external beam radiation therapy for partial breast irradiation or other therapies. The localization system 10 can include a controller 80 and a field device 60, 70 (e.g., including an excitation source 60 and a sensor assembly 70). The field device 60, 70 can generate one or more alternating magnetic fields that the active markers 40 sense, or the field device 60, 70 can sense one or more alternating magnetic fields generated by the active markers 40. In either case, the controller 80 receives location signals from either the field device 60, 70 or the active markers 40 and determines the actual location of the individual markers 40 in a three-dimensional reference frame when the markers are within or on the patient 6. In a particular embodiment of the system illustrated in FIG. 1, the localization system 10 tracks the three-dimensional coordinates of the markers 40 in real time to an absolute external reference frame during the setup process and while irradiating the patient to mitigate collateral effects on adjacent healthy tissue and to ensure that the desired dosage is applied to the target tissue.

In the embodiment shown in FIG. 1, the system 10 has removable implantable devices 20 implanted in a patient 6 relative to a resection cavity 7. Each implantable device 20 can include the removable device 30 and the marker 40 contained within the removable device 30. In the embodiment shown in FIG. 1, the implantable devices 20a-b include markers 40a-d, respectively. The markers 40 can be active markers configured to transmit independent location signals in response to an energy source located external to the body of the patient (e.g., outside the dermis of the patient). For example, the markers 40 can be wireless active sensors that wirelessly transmit location signals in response to wirelessly transmitted excitation signals. Such wireless active markers can comprise a magnetic transponder as described in U.S. patent application Ser. Nos. 11/243,478 and 11/166,801, both of which are incorporated herein by reference in their entirety. The excitation source 60 of the localization system 10 is configured to wirelessly transmit excitation signals to the markers 40, and the sensor assembly 70 is configured to measure the location signals wirelessly transmitted from the markers 40.

In several embodiments, one or more removable implantable devices 20 are implanted in the patient 6 such that the markers 40 are at least proximate to the resection cavity 7. The removable implantable devices 20 are accordingly associated with the resection cavity such that the implantable device and the markers contained therein move based on the position, rotation, and/or expansion-contraction of the resection cavity 7. In the embodiment shown in FIG. 1, the two markers 40b and 40c are associated with each removable implantable device, but a single marker, two markers, or more than three markers can be used depending on the particular application. Two markers, for example, may be desirable because the target can be located accurately and the relative displacement between the markers over time can be used to monitor the status and position of the resection cavity 7.

The localization system 10 determines the actual location of the markers 40 in a three-dimensional reference frame when the markers are within or on the patient 6. In a particular embodiment of the system 10 illustrated in FIG. 1, the localization system 10 tracks the three-dimensional coordinates of the markers 40 in real time to an absolute external reference frame during the setup process and while irradiating the patient to mitigate collateral effects on adjacent tissue outside the treatment margin and to ensure that the desired dosage is applied to the target tissue.

Several embodiments of the implantable device 20 for guided radiation therapy comprises an active marker having a circuit configured to be contained in an external sheath which is implanted in a patient and to transmit a wirelessly transmitted location signal from within the patient in response to a wirelessly transmitted source energy. In an alternative embodiment, the active marker transmits a location signal along a wire. The implantable device can further include a fastening unit for retaining the marker in a fixed position in the external sheath. The marker, for example, can comprise a leadless marker having a circuit with a core and a coil around the core.

Several embodiments of the implantable device 20 enable accurate determination of the size of the resection cavity 7 within the breast of the patient without taking expensive CT images and manually assessing the images. This aspect is very useful because the shape and size of the resection cavity 7 may change over the course of the treatment. This change could cause the external beam radiation to irradiate healthy tissue but miss targeted tissue. By localizing the relative positions of the markers 40, changes in the size and shape of the resection cavity 7 can be determined before, during, and after each treatment session to ensure that the desired dose of radiation is accurately delivered to the correct tissue.

Several embodiments of the implantable device 20 can also track movement of the resection cavity or other treatment target throughout the course of therapy to accurately deliver external beam radiation within the treatment margin. Breast tissue, for example, is soft and pliable such that it may be difficult to hold the treatment target at the isocenter of the external radiation beam. The breast is also likely to move during treatment because of thoracic expansion/contraction caused by respiration. Several embodiments of the implantable device 20 are also useful for detecting movement of the patient or other displacement of the breast in real time during therapy. As a result, the implantable device 20 is expected to provide accurate measurements to confirm the status and the location of the treatment target throughout the course of therapy.

Several embodiments of the implantable device 20 also track the rotational orientation of the resection cavity or other target site relative to the body or the radiation beam throughout the course of treatment. The rotational orientation of the target site may be important in several applications because resection cavities and other targets are generally not spherical such that the rotational orientation affects the profile of the treatment margin relative to the position of the external beam. The markers 40 can be tracked or otherwise located using the localization system 10 to determine rotational orientation of the target relative to the external beam.

Several embodiments of an implantable device 20 for guided radiation therapy comprise an active marker configured to be pre-loaded into a catheter; the catheter is configured to be removeably implanted in the tissue of a patient. The marker transmits a non-ionizing wireless signal in response to a non-ionizing wirelessly transmitted source energy. The implantable device can further include a stability element coupled to the marker and an explant line. The stability element is configured to hold the marker at fixed location within the catheter (e.g., known location) with respect to a target in the tissue. The explant line has a first portion coupled to the marker and/or the stability element and a second portion configured to be at least proximate to the dermis of the patient.

Additional localization and tracking systems are described in U.S. patent and patent application Ser. No. 10/438,550 filed May 14, 2003; U.S. Pat. No. 6,363,940 issued Apr. 2, 2002; U.S. Pat. No. 6,918,919 issued Jul. 19, 2005; U.S. Pat. No. 6,675,810 issued Jan. 13, 2004; Ser. No. 09/877,498 field Jun. 8, 2001; U.S. Pat. No. 7,135,978 issued Nov. 14, 2006; U.S. Pat. No. 6,812,842 issued Nov. 2, 2004; U.S. Pat. No. 6,838,990 issued Jan. 4, 2005; U.S. Pat. No. 6,822,570 issued Nov. 23, 2004; Ser. No. 10/679,801 filed October; and Ser. No. 10/745,097 herein incorporated in their entirety by reference.

A. Basic Devices

1. Removable Implant

Figure 3:
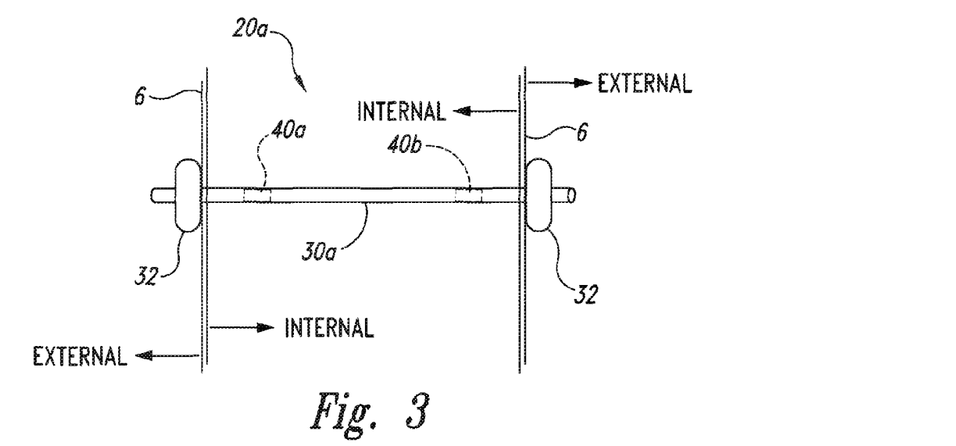
FIGS. 3-6 are side views of removable implantable devices configured in accordance with embodiments of the present technology.
Figure 5:
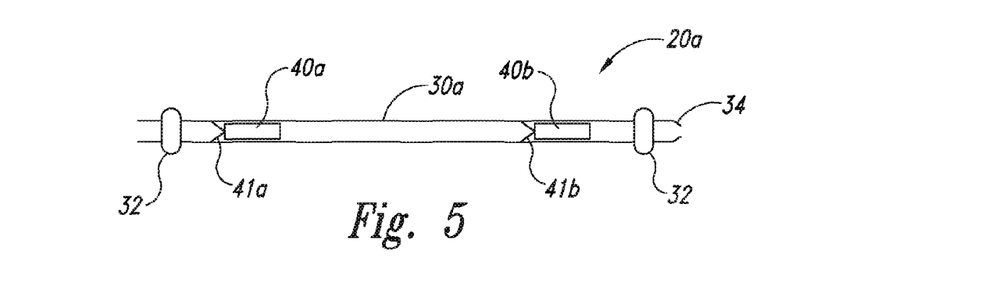

According to aspects of the disclosure, a system for fiducials contained in a removable device for use in radiation therapy includes a removable implant device having a cavity configured to receive a fiducial or marker. As shown in FIG. 3, the removable implant 20a may for example be a sheath 30a, a capsule, or a catheter with an internal lumen that is suitable for implantation into human tissue and permits subsequent removal. As shown in FIG. 5, additional removable implant or external sheath features include a sheath having a distal tip 34 with a decreasing diameter to facilitate percutaneous insertion, for example, a tip design such as a "missile-shaped tip", to facilitate tissue penetration. According to further aspects of the disclosure, the sheath may have leading or trailing components from the tip of lesser diameter that can be used as a "thread." According to still further aspects of the disclosure, the removable implant may include micro-perforations such that a liquid-contrast may be used to locate the implant.

2. Positioning Device

Figure 4:
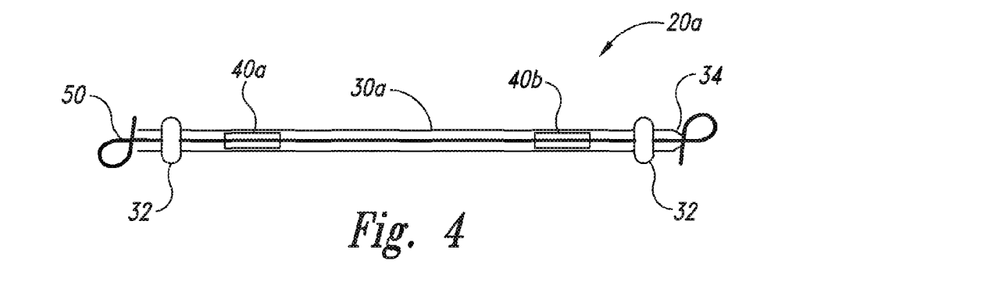
Figure 6:
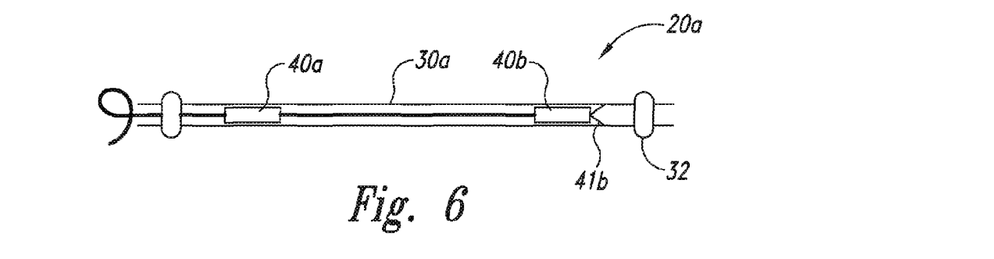

As shown in FIGS. 4 and 6, a positioning device 50, such as a plastic or nitinol filament or tether, affixed to at least one of a fiducial 40a, 40b. Alternatively, the positioning device may be preformed indents or detents in an interior lumen or cavity of a catheter or external sheath. Alternatively, the positioning device may be a liquid or gel filling the cavity of the removable implant. According to further alternative aspects, the positioning device may include a fastener 41a, 41b (FIG. 5) which retains markers 40a, 40b respectively in position within the removable implant. The positioning device may be preloaded, inserted simultaneously, or afterloaded into the removable device or fiducial sheath. According to further aspects of the disclosure, additional filament features include: pre-attachment of one or more fiducials suitable for radiation therapy localization and continuous tracking; may contain one or more special markers that are optimized for imaging, such as ultrasound; may be positioned to a desired location within the sheath by the operators; may be self-coiling such that those portions of the filament protruding from the sheath can assume a low-profile on the skin; and may be fixed to the sheath.

3. Fiducials

As shown in FIGS. 3-6, one or more fiducials or active markers 40, such as an electronic transponder, gold markers, or infrared reflectors, can be configured to be embedded, attached, or contained within an implantable, removable device such as an external sheath. According to alternative aspects of the disclosure, the fiducials are secured to the positioning device or filament such that in operation, the fiducial is moveable within the external sheath. According to further aspects of the disclosure, the fiducials are suitable to enable localization and continuous tracking during radiation therapy. According to still further aspects, the fiducial or the filament may be imagable by ultrasound, x-ray, or magnetic resonance when inside the sheath.

4. External Sheath Fasteners

As shown in FIGS. 3-6, a retention device 32, such as a plastic disk or other low-profile securing element, can be slipped over or around the sheath and/or filament and then secured to the patient surface by, for example, a temporary adhesive to hold the sheath and filament in a stable position within the tissue. According to further aspects of the retention device 32, a fastener feature may include a reversible release mechanism for use in repositioning the filament. Yet another aspect of the retention device 32 is to provide a low-profile device to maintain patient comfort during use.

5. Markers

Figure 7:
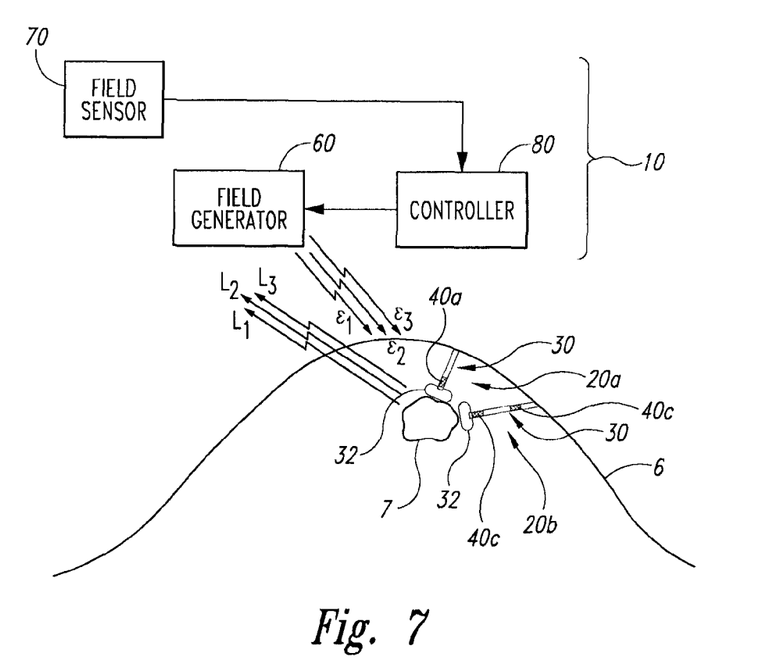
FIG. 7 is a partially schematic view illustrating the operation of a localization system configured in accordance with embodiments of the present technology.

FIG. 7 is a schematic view illustrating the operation of an embodiment of the localization system 10 and markers 40a-c for treating a target in the breast of the patient. The markers 40a-c are used to determine the location, orientation, shape, size, and/or other parameter of a resection cavity or other target before, during, and after radiation sessions. More specifically, the localization system 10 determines the locations of the markers 40a-c and provides objective target position data to a memory, user interface, linear accelerator, and/or other devices in real time during setup, treatment, deployment, simulation, surgery, and/or other medical procedures. In one embodiment of the localization system, real time means that indicia of objective coordinates are provided to a user interface at (a) a sufficiently high refresh rate (i.e., frequency) such that pauses in the data are not humanly discernable and (b) a sufficiently low latency to be at least substantially contemporaneous with the measurement of the original signal. In other embodiments, real time is defined by higher frequency ranges and lower latency ranges for providing the objective data, or in still other embodiments, real time is defined as providing objective data responsive to the location of the markers (e.g., at a periodicity or frequency that adequately tracks the location of the target in real time and/or at a latency that is at least substantially contemporaneous with obtaining position data of the markers).

The excitation source 60 (e.g., pulsed magnetic field generator), sensor assembly 70, and controller 80 operate together to localize the markers 40. The excitation source 60 generates an excitation energy to energize at least one of the markers 40a-c in the patient 6. The embodiment of the excitation source 60 shown in FIG. 5 produces a pulsed magnetic field at different frequencies. For example, the excitation source 60 can frequency multiplex the magnetic field at a first frequency E1 to energize the first marker 40a, a second frequency E2 to energize the second marker 40b, and a third frequency E3 to energize the third marker 40c. In response to the excitation energy, the markers 40a-c generate location signals L1-3 at unique response frequencies. More specifically, the first marker 40a generates a first location signal L1 at a first frequency in response to the excitation energy at the first frequency E1, the second marker 40b generates a second location signal L2 at a second frequency in response to the excitation energy at the second frequency E2, and the third marker 40c generates a third location signal L3 at a third frequency in response to the excitation energy at the third frequency E3. In an alternative embodiment with two markers, the excitation source generates the magnetic field at frequencies E1 and E2, and the markers 40a-b generate location signals L1 and L2, respectively.

The sensor assembly 70 can include a plurality of coils to sense the location signals L1-3 from the markers 40a-c. The sensor assembly 70 can be a flat panel having a plurality of coils that are at least substantially coplanar relative to each other. In other embodiments, the sensor assembly 70 may be a non-planar array of coils.

The controller 80 includes hardware, software, or other computer-operable media containing instructions that operate the excitation source 60 to multiplex the excitation energy at the different frequencies E1-3. For example, the controller 80 causes the excitation source 60 to generate the excitation energy at the first frequency E1 for a first excitation period, and then the controller 80 causes the excitation source 60 to terminate the excitation energy at the first frequency E1 for a first sensing phase during which the sensor assembly 70 senses the first location signal L1 from the first marker 40a without the presence of the excitation energy at the first frequency E1. The controller 80 then causes the excitation source 60 to (a) generate the second excitation energy at the second frequency E2 for a second excitation period; and (b) terminate the excitation energy at the second frequency E2 for a second sensing phase during which the sensor assembly 70 senses the second location signal L2 from the second marker 40b without the presence of the second excitation energy at the second frequency E2. The controller 80 then repeats this operation with the third excitation energy at the third frequency E3 such that the third marker 40c transmits the third location signal L3 to the sensor assembly 70 during a third sensing phase. As such, the excitation source 60 wirelessly transmits the excitation energy in the form of pulsed magnetic fields at the resonant frequencies of the markers 40a-c during excitation periods, and the markers 40a-c wirelessly transmit the location signals L1-3 to the sensor assembly 70 during sensing phases. It will be appreciated that the excitation and sensing phases can be repeated to permit averaging of the sensed signals to reduce noise.

The computer-operable media in the controller 80, or in a separate signal processor, also includes instructions to determine the absolute positions of each of the markers 40a-c in a three-dimensional reference frame. Based on signals provided by the sensor assembly 70 that correspond to the magnitude of each of the location signals L1-3, the controller 80 and/or a separate signal processor calculates the absolute coordinates of each of the markers 40a-c in the three-dimensional reference frame.

The embodiments of systems and implantable devices for guided radiation therapy described above can be used in methods for treating a patient after a procedure that leaves a resection cavity within the patient. An embodiment of such a method comprises implanting an active marker in tissue of the patient at the resection cavity, wherein the active marker is configured to transmit a non-ionizing wireless signal in response to a non-ionizing wirelessly transmitted source energy, and wherein the marker is coupled to a fastening unit having a distal first portion and a proximal second portion. The method can further include securing the second portion of the fastening unit at least proximate to the dermis of the patient, and localizing the active marker by wirelessly transmitting a non-ionizing source energy to the active marker, transmitting a non-ionizing location signal from the active marker in response to the source energy, and calculating a position of the active marker in an external coordinate system based on the location signal.

B. Real Time Tracking

The localization system 10 and markers 40 enable real time tracking of the target and/or status of the resection cavity or other target relative to an external reference frame outside the patient during treatment planning, setup, irradiation sessions, and other times of the radiation therapy process. In many embodiments, real time tracking means collecting position data of the markers, determining the locations of the markers in an external reference frame (i.e., a reference frame outside the patient), and providing an objective output in the external reference frame responsive to the location of the markers. The objective output is provided at a frequency/periodicity that adequately tracks the target in real time and/or a latency that is at least substantially contemporaneous with collecting the position data (e.g., within a generally concurrent period of time).

For example, several embodiments of real time tracking are defined as determining the locations of the markers and calculating the locations relative to an external reference frame at (a) a sufficiently high frequency/periodicity so that pauses in representations of the target location at a user interface do not interrupt the procedure or are readily discernable by a human, and (b) a sufficiently low latency to be at least substantially contemporaneous with the measurement of the location signals from the markers. Alternatively, real time means that the localization system 10 calculates the absolute position of each individual marker 40 and/or the location of the target at a periodicity of approximately 1 ms to 5 seconds, or in many applications at a periodicity of approximately 10-100 ms, or in some specific applications at a periodicity of approximately 20-50 ms. In applications for user interfaces, for example, the periodicity can be 12.5 ms (i.e., a frequency of 80 Hz), 16.667 ms (60 Hz), 20 ms (50 Hz), and/or 50 ms (20 Hz). Additionally, real time tracking can further mean that the localization system 10 provides the absolute locations of the markers 40 and/or the target to a memory device, user interface, linear accelerator, or other device within a latency of 10 ms to 5 seconds from the time the localization signals were transmitted from the markers 40. In more specific applications, the localization system 10 generally provides the locations of the markers 40, target, or an instrument within a latency of about 20-50 ms. The localization system 10 accordingly provides real time tracking to monitor the position of the markers 40 and/or the target with respect to an external reference frame in a manner that is expected to enhance the efficacy of radiation therapy.

Alternatively, real time tracking can further mean that the localization system 10 provides the absolute locations of the markers 40 and/or the target to a memory device, user interface, or other device within a latency of 10 ms to 5 seconds from the time the localization signals were transmitted from the markers 40. In more specific applications, the location system generally provides the locations of the markers 40 and/or target within a latency of about 20-50 ms. The localization system 10 accordingly provides real time tracking to monitor the position of the markers 40 and/or the target with respect to an external reference frame in a manner that is expected to enhance the efficacy of radiation therapy because higher radiation doses can be applied to the target and collateral effects to healthy tissue can be mitigated.

Alternatively, real-time tracking can further be defined by the tracking error. Measurements of the position of a moving target are subject to motion-induced error, generally referred to as a tracking error. According to specific embodiments, the localization system 10 and at least one marker 40 enable real time tracking of the target or other instrument relative to an external reference frame with a tracking error that is within clinically meaningful limits.

Tracking errors are due to two limitations exhibited by any practical measurement system, specifically (a) latency between the time the target position is sensed and the time the position measurement is made available, and (b) sampling delay due to the periodicity of measurements. For example, if a target is moving at 5 cm/s and a measurement system has a latency of 200 ms, then position measurements will be in error by 1 cm. The error in this example is due to latency alone, independent of any other measurement errors, and is simply due to the fact that the target or instrument has moved between the time its position is sensed and the time the position measurement is made available for use. If the measurement system further has a sampling periodicity of 200 ms (i.e., a sampling frequency of 5 Hz), then the peak tracking error increases to 2 cm, with an average tracking error of 1.5 cm.

For a real time tracking system to be useful in medical applications, it is desirable to keep the tracking error within clinically meaningful limits. For example, in a system for tracking motion of a tumor or an instrument for radiation therapy, it may be desirable to keep the tracking error within 5 mm. Acceptable tracking errors may be smaller when tracking other organs for radiation therapy. In accordance with aspects of the present invention, real time tracking refers to measurement of target position and/or rotation with tracking errors that are within clinically meaningful limits.

B. Basic System Methods

1. Target Identification and Approximate Geometric Center (AGC) Determination

The radiation target, such as a lumpectomy cavity in the breast, may be identified by a traditional imaging technique, for example, by ultrasound. The approximate geometric center (AGC) of the target is roughly determined by the operators, potentially assisted by imaging software tools. One or more reference points to the AGC on the patient's skin can be placed. The insertion trajectories about the AGC for the fiducial sheath are determined by the operators, such that the sheaths when placed will be in general proximity to the AGC. Entrance and exit sites for the sheaths on the skin will be selected. In addition, one could envision a sheath placed into the lumpectomy cavity for purposes of injecting contrast into the cavity or removing fluid from that cavity.

2. Sheath Insertion

An appropriate anesthetic, if needed, is administered to the patient by the surgeon, such as a lidocaine infiltration at the entrance and exit points on the skin and along the projected insertion path. Next, a needle is passed from an entrance point on the skin to its corresponding skin exit point. The sheath (or tail component) is then threaded into the needle. The insertion needle and sheath assembly is then pulled through the tissue. The "missile tip" of the sheath facilitates skin and tissue penetration. Continuous or repeated imaging can be conducted to assess the sheath position relative to the target or GC. The skin fastener can next be applied to provide initial sheath stabilization within the tissue, taking care not to occlude the sheath lumen. The sheath portions protruding from the skin can be trimmed to the desired length. One or more sheaths could be inserted.

3. Filament Afterloading and Positioning

In one embodiment, a filament containing an array of fiducials or specialized markers is then threaded into the sheath. Alternatively, the markers may be pre-loaded or an alternative marker positioning device may be employed to place the markers relative to the removable implant. The filament is positioned such that the fiducials are in proximity to the AGC. This can be assisted by imaging, for example, by ultrasound. For example, an ultrasound image plane through the AGC and the sheath is obtained by the operator. Next, the filament is pulled through the plane until a desired point of that filament is reached as demarked by an ultrasonic marker (which can be the fiducial or a separate marker).

4. Filament Fixation

After the operators have positioned the filament within the removable device, shown in the Figures as a sheath, to their initial satisfaction, an action is applied to the fastener such that the filament is secured within the sheath to prevent subsequent filament movement. Excess filament protruding from the sheath can be trimmed, if desired. A temporary dressing can be placed over the fastener and protruding filament.

5. Radiation Therapy Treatment Planning and Possible Re-Positioning

At the appropriate time following sheath and fiducial, the patient undergoes standard radiation planning simulation. At simulation an image, usually a CT scan, is obtained. A preliminary assessment of the target is obtained. If desired, contrast can be injected into the cavity through one or more of the sheaths to facilitate imaging of the cavity. If after a preliminary assessment of the fiducial relationship to the target AGC indicates a need for better alignment, the fastener can be loosened sufficiently to allow the filament to be repositioned. Once it's determined that fiducial position relative to the AGC is satisfactory, the fastener is closed to secure the filament within the sheath. This realignment process can be made one or more time during the course of radiation therapy should it be necessary.

6. Radiation Therapy Delivery

The prescribed course of radiation therapy is delivered. The fiducials are used to setup and continuously track the patient during treatment. In addition, the fiducials can be used to adapt the radiation to the patient. For example, if the distances between the fiducials changes, they might suggest that there has been some deformation of the target, such as swelling of the lumpectomy cavity. This change may suggest that repeat simulation and re-planning might be indicated. One could envision other adaptations that could be invoked dependent on fiducial tracking. For example, if the patient exhibits excess breathing motion, the radiation could be gated, or a bio-feedback program invoked.

7. Removal

Once the prescribed course of radiation is delivered, the fasteners are released and the sheath containing the fiducial filament is removed. According to alternative embodiments, the removable implant is removed concurrent with the marker removal.

Additional Embodiments of Apparatus for Facilitating Radiation Treatment

Figure 8:
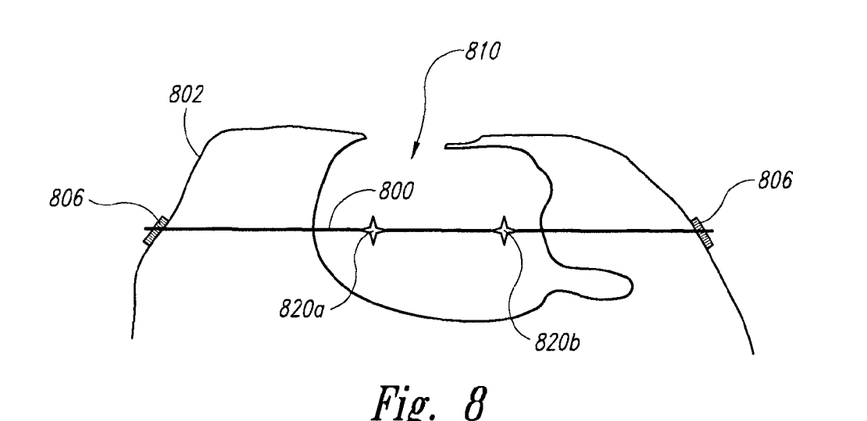
FIG. 8 is a side view of a removable implantable device anchored across a resection cavity in accordance with embodiments of the present technology.

As shown in FIG. 8, one or more catheters 800 is anchored on breast surface 802 that pass such that the catheters 800 pass through a cavity 810. In operation, tension on the catheter 800 prevents movement. Similar to interstitial breast brachytherapy; this configuration can be done at time of biopsy or via ultrasound. Furthermore, cavity shrinkage or expansion can be adjusted for cinching buttons 806. Additionally, this configuration is operationally quite simple or from a regulator perspective, a 510K may be obtained (predicate is breast brachytherapy, existing FDA approved brachycaths). According to aspects of this disclosure, transponders 820a, 820b could be after-loaded into catheter to be at COM. According to further aspects of this disclosure, the catheter 800 may be rigid or semi-rigid.

Figure 9:
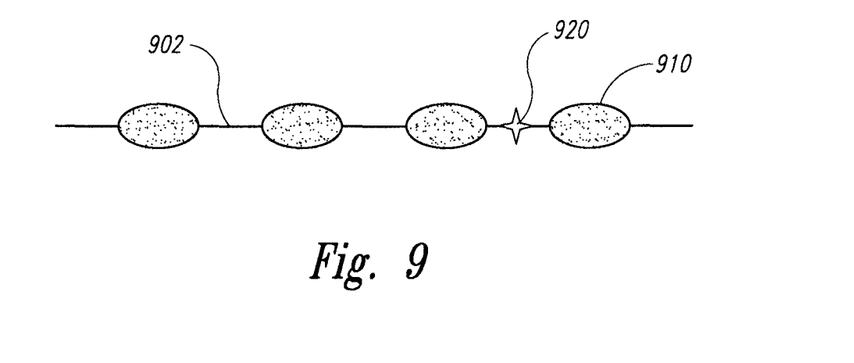
FIG. 9 is a side view of a removable implantable device configured in accordance with embodiments of the present technology.

As shown in FIG. 9, an alternative embodiment includes a flexible train of repeating interconnectors 902 and capsules 910. The capsules 910 may be semi-rigid so as not to be deformable; and may further be potentially filled with an imaging agent or composed of a radiographic visible material. The interconnectors 902 may be flexible, so as to let the capsules fold upon themselves; sufficiently strong so as to be removable. According to further aspects of the disclosure, marker or transponders 920 may be embedded in capsule 902 or interconnector 910.

Figure 10:
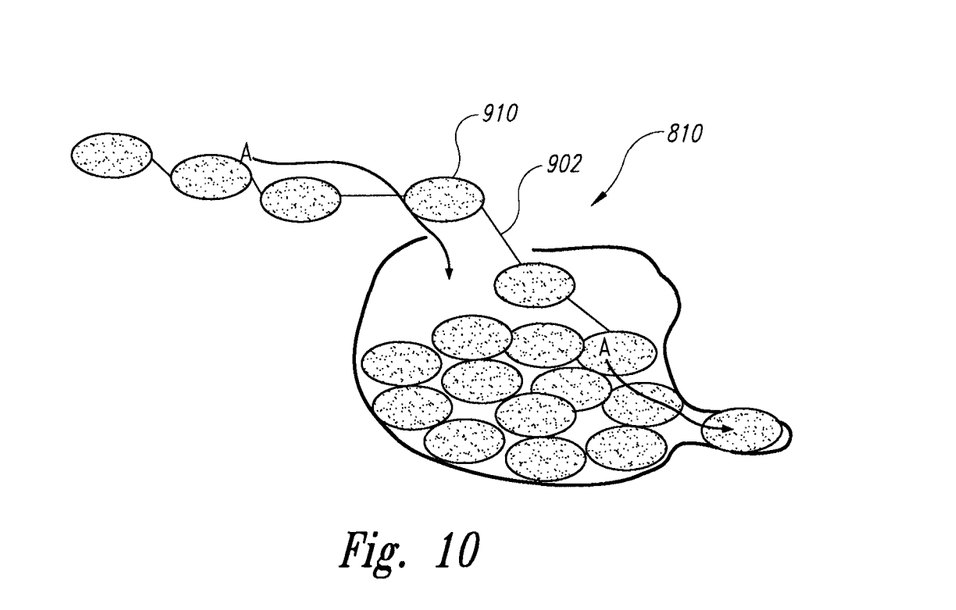
FIGS. 10-12 are a series of side views illustration implantation of the removable implantable device of FIG. 9 in a soft tissue cavity in accordance with embodiments of the present technology.
Figure 11:
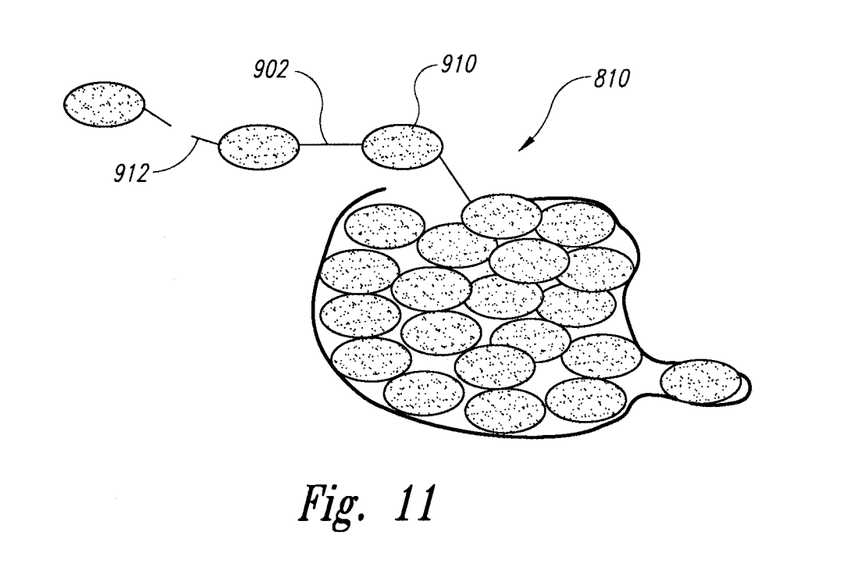
Figure 12:
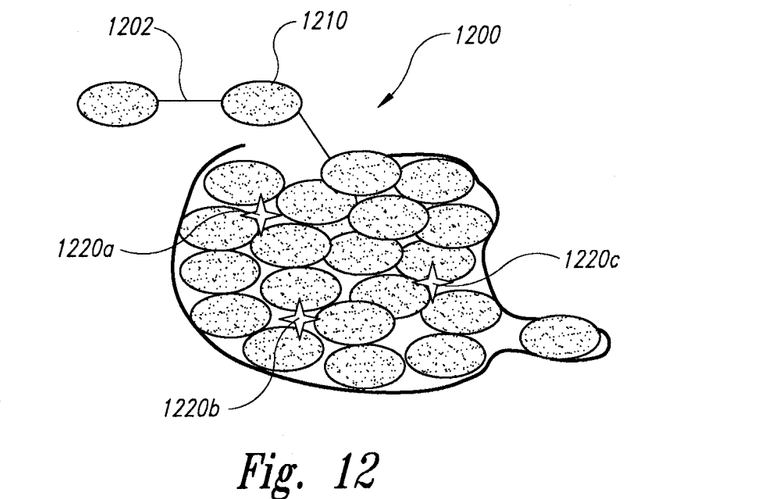

As shown in FIG. 10, irregular soft tissue cavity created by a surgical procedure is filled with a string of capsules. In operation, the surgeon fills the cavity with the device shown in FIG. 9, taking care to pack any crevices. As shown in FIG. 11, the excess is trimmed once the cavity is filled. In operation, the device serves to smooth and maintain the shape of the cavity. Capsules outline cavity boundaries on a subsequent imaging study. Capsules can be radiopague or filled with an imaging agent. As shown in FIG. 12, the capsules or interconnectors could have transponders integrated into them to guide external beam irradiation.

From the foregoing, it will be appreciated that specific embodiments of the invention have been described herein for purposes of illustration, but well-known structures and functions have not been shown or described in detail to avoid unnecessarily obscuring the description of the embodiments of the invention. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of features are not precluded. It will also be appreciated that specific embodiments of the invention have been described herein for purposes of illustration, but that various modifications may be made without deviating from the inventions. For example, many of the elements of one of embodiment can be combined with other embodiments in addition to, or in lieu of, the elements of the other embodiments. Accordingly, the invention is not limited except as by the appended claims.

We claim:

1. An implantable device for guided radiation therapy, comprising:
   a removable implantable device having a first portion configured to be implanted in tissue of a patient and opposing end portions configured to remain external to the patient on two sides of a resection cavity, wherein the first portion includes a predefined cavity extending from one of the opposing end portions to another of the opposing end portions;
   an active marker contained within the predefined cavity of the first portion, the marker having a circuit configured to transmit a wirelessly transmitted location signal from within the patient, wherein the marker is configured to be received in the predefined cavity via one of the opposing end portions;
   a first fastener coupled to one of the opposing end portions of the removable implantable device and having a portion configured to be external to the patient at least proximate to a dermis of the patient; and
   a second fastener coupled to another of the opposing end portions of the removable implantable device and having a portion configured to be external to the patient at least proximate to a dermis of the patient, wherein the first and second fasteners are configured to place the removable implantable device under tension between the opposing end portions to adjust for shrinkage or expansion of the resection cavity, and wherein the removable device, the active marker, and the first and second fasteners are configured to remain implanted in the patient during external beam radiation therapy.

2. The device of claim 1 wherein the active marker is one of a plurality of active markers.

3. The device of claim 1 wherein the active marker comprises a wired marker having a casing and a core within the casing, and wherein the circuit comprises a coil within the casing around the core.

4. The device of claim 1 wherein the active marker comprises a leadless marker having a casing and a core within the casing, and wherein the circuit comprises a coil within the casing around the core.

5. The device of claim 1, further comprising a stability element coupled to the active marker and configured to fix the active marker at a fixed location within the predefined cavity of the removable implantable device.

6. The device of claim 1, further comprising a tether extending into the predefined cavity and coupled to the active marker and at least one of the first and the second fasteners, wherein the at least one first and second fasteners is configured to hold the tether in a stable position within the tissue.

7. The device of claim 6 wherein the tether is a filament.

8. The device of claim 1 wherein the removable implantable device is a sheath.

9. The device of claim 1 wherein the removable implantable device is a catheter.

10. The device of claim 1 wherein the removable implantable device is a capsule.

11. The device of claim 1 wherein the removable implantable device is a plurality of capsules.

12. The device of claim 1 wherein the removable implantable device is a plurality of interconnected capsules.

13. A method for tracking a target site in a patient after a procedure that leaves a resection cavity within the patient, the method comprising:
   inserting a portion of an implantable device into the resection cavity, wherein the implantable device has opposing end portions and is configured to remain implanted in the patient during external beam radiation therapy,
      wherein inserting the portion of the implantable device into the resection cavity comprises passing the implantable device through the resection cavity such that the opposing end portions of the implantable device are positioned external to the patient on two sides of the resection cavity, and wherein the implantable device is under tension between the opposing end portions to adjust for shrinkage or expansion of the resection cavity,
   inserting an active marker affixed to a first portion of an explant line into a lumen of the implantable device after the implantable device has been implanted in the patient such that the active marker is positioned at least proximate to the resection cavity, wherein the explant line has a second portion configured to extend outside the patient after the active marker and the first portion of the explant line are implanted; and
   localizing the active marker positioned within the patient relative to the implantable device by transmitting a non-ionizing location signal from the active marker and calculating a position of the active marker in an external coordinate system based on the location signal.

14. A method for tracking a target site in a patient after a procedure that leaves a resection cavity within the patient, the method comprising:
   passing an implantable device through the resection cavity such that opposing end portions of the implantable device are positioned external to the patient on two sides of the resection cavity and a portion of the implantable device is in the resection cavity, wherein the implantable device is under tension between the opposing ends to adjust for shrinkage or expansion of the resection cavity, and wherein the implantable device is configured to remain implanted in the patient during external beam radiation therapy;
   inserting an active marker into a lumen of the implantable device after the implantable device has been implanted in the patient such that the active marker is positioned at least proximate to the resection cavity; and
   localizing the active marker positioned within the patient relative to the implantable device by transmitting a non-ionizing location signal from the active marker and calculating a position of the active marker in an external coordinate system based on the location signal.

15. The method of claim 14, further comprising adjusting cinching buttons on the opposing ends of the implantable device to place the implantable device under tension as the resection cavity shrinks or expands.

* * * * *